United States Patent
Lechmann et al.

(10) Patent No.: US 8,764,831 B2
(45) Date of Patent: *Jul. 1, 2014

(54) INTERVERTEBRAL IMPLANT

(75) Inventors: Beat Lechmann, Bettlach (CH); Dominique Burkard, Gretzenbach (CH); Chris M. J. Cain, Norwood (AU); Claude Mathieu, Zurich (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/969,330

(22) Filed: Dec. 15, 2010

(65) Prior Publication Data

US 2011/0087327 A1 Apr. 14, 2011

Related U.S. Application Data

(63) Continuation of application No. 12/432,088, filed on Apr. 29, 2009, now Pat. No. 7,862,616, which is a continuation of application No. 11/199,599, filed on Aug. 8, 2005, now Pat. No. 7,846,207, which is a continuation of application No. PCT/CH03/00089, filed on Feb. 6, 2003.

(51) Int. Cl.
*A61F 2/44* (2006.01)

(52) U.S. Cl.
USPC ............................... 623/17.12; 623/17.11

(58) Field of Classification Search
USPC ............................ 623/17.11–17.16
See application file for complete search history.

(56) References Cited

U.S. PATENT DOCUMENTS

| | | |
|---|---|---|
| 1,105,105 A | 7/1914 | Sherman |
| 2,621,145 A | 12/1952 | Sano |
| 4,135,506 A | 1/1979 | Ulrich |
| 4,501,269 A | 2/1985 | Bagby |
| 4,503,848 A | 3/1985 | Caspar et al. |
| 4,512,038 A | 4/1985 | Alexander et al. |
| 4,599,086 A | 7/1986 | Doty |
| 4,627,853 A | 12/1986 | Campbell et al. |
| 4,678,470 A | 7/1987 | Nashef et al. |
| 4,717,115 A | 1/1988 | Schmitz et al. |
| 4,858,603 A | 8/1989 | Clemow et al. |
| 4,904,261 A | 2/1990 | Dove et al. |
| 4,936,851 A | 6/1990 | Fox et al. |
| 4,950,296 A | 8/1990 | McIntyre |

(Continued)

FOREIGN PATENT DOCUMENTS

| | | |
|---|---|---|
| CA | 2317791 A1 | 8/1999 |
| DE | 30 42 003 A1 | 7/1982 |

(Continued)

OTHER PUBLICATIONS

U.S. Appl. No. 11/199,599: Amendment/Request for Reconsideration after Non-Final Rejection, dated Sep. 29, 2009, 30 pages.

(Continued)

*Primary Examiner* — Pedro Philogene
*Assistant Examiner* — Lynnsy Schneider
(74) *Attorney, Agent, or Firm* — Baker & Hostetler LLP

(57) ABSTRACT

An intervertebral implant having a three-dimensional body and a securing plate. The intervertebral implant also includes a front plate (8) displaceably disposed as an insert with a front side of the three-dimensional body.

43 Claims, 6 Drawing Sheets

(56) References Cited

U.S. PATENT DOCUMENTS

| | | | |
|---|---|---|---|
| 4,955,908 | A | 9/1990 | Frey et al. |
| 4,961,740 | A | 10/1990 | Ray et al. |
| 4,978,350 | A | 12/1990 | Wagenknecht |
| 4,994,084 | A | 2/1991 | Brennan |
| 5,026,373 | A | 6/1991 | Ray et al. |
| 5,053,049 | A | 10/1991 | Campbell |
| 5,062,850 | A | 11/1991 | MacMillan et al. |
| 5,084,051 | A | 1/1992 | Tormala et al. |
| 5,085,660 | A | 2/1992 | Lin |
| 5,112,354 | A | 5/1992 | Sires |
| 5,180,381 | A | 1/1993 | Aust et al. |
| 5,192,327 | A | 3/1993 | Brantigan |
| 5,211,664 | A | 5/1993 | Tepic et al. |
| 5,235,034 | A | 8/1993 | Bobsein et al. |
| 5,275,601 | A | 1/1994 | Gogolewski et al. |
| 5,281,226 | A | 1/1994 | Davydov et al. |
| 5,284,655 | A | 2/1994 | Bogdansky et al. |
| 5,290,312 | A | 3/1994 | Kojimoto et al. |
| 5,298,254 | A | 3/1994 | Prewett et al. |
| 5,314,476 | A | 5/1994 | Prewett et al. |
| 5,314,477 | A | 5/1994 | Marnay |
| 5,348,788 | A | 9/1994 | White |
| 5,397,364 | A * | 3/1995 | Kozak et al. ............... 623/17.11 |
| 5,405,391 | A | 4/1995 | Hednerson et al. |
| 5,423,817 | A | 6/1995 | Lin |
| 5,439,684 | A | 8/1995 | Prewett et al. |
| 5,458,638 | A | 10/1995 | Kuslich et al. |
| 5,458,641 | A | 10/1995 | Ramirez Jimenez |
| 5,489,308 | A | 2/1996 | Kuslich et al. |
| 5,507,818 | A | 4/1996 | McLaughlin |
| 5,514,180 | A | 5/1996 | Heggeness et al. |
| 5,520,690 | A | 5/1996 | Errico et al. |
| 5,522,899 | A | 6/1996 | Michelson |
| 5,531,746 | A | 7/1996 | Errico et al. |
| 5,534,030 | A | 7/1996 | Navarro et al. |
| 5,534,031 | A | 7/1996 | Matsuzaki et al. |
| 5,549,612 | A | 8/1996 | Yapp et al. |
| 5,549,679 | A | 8/1996 | Kuslich |
| 5,554,191 | A | 9/1996 | Lahille et al. |
| 5,556,430 | A | 9/1996 | Gendler |
| 5,569,308 | A | 10/1996 | Sottosanti |
| 5,571,190 | A | 11/1996 | Ulrich et al. |
| 5,571,192 | A | 11/1996 | Schonhoffer |
| 5,593,409 | A | 1/1997 | Michelson |
| 5,601,553 | A | 2/1997 | Trebing et al. |
| 5,607,474 | A | 3/1997 | Athanasiou et al. |
| 5,609,635 | A * | 3/1997 | Michelson ................. 623/17.16 |
| 5,609,636 | A | 3/1997 | Kohrs et al. |
| 5,609,637 | A | 3/1997 | Biedermann et al. |
| 5,616,144 | A | 4/1997 | Yapp et al. |
| 5,676,699 | A | 10/1997 | Gogolewski et al. |
| 5,683,394 | A | 11/1997 | Rinner |
| 5,683,463 | A | 11/1997 | Godefroy et al. |
| 5,702,449 | A | 12/1997 | McKay |
| 5,702,451 | A | 12/1997 | Biedermann et al. |
| 5,702,453 | A | 12/1997 | Rabbe et al. |
| 5,702,455 | A | 12/1997 | Saggar |
| 5,713,899 | A | 2/1998 | Marnay et al. |
| 5,728,159 | A | 3/1998 | Stroever et al. |
| 5,735,905 | A | 4/1998 | Parr |
| 5,755,796 | A | 5/1998 | Ibo et al. |
| 5,766,253 | A | 6/1998 | Brosnahan, III |
| 5,776,194 | A | 7/1998 | Mikol et al. |
| 5,776,196 | A | 7/1998 | Matsuzaki et al. |
| 5,776,197 | A | 7/1998 | Rabbe et al. |
| 5,776,198 | A | 7/1998 | Rabbe et al. |
| 5,776,199 | A | 7/1998 | Michelson |
| 5,782,915 | A | 7/1998 | Stone |
| 5,785,710 | A | 7/1998 | Michelson |
| 5,800,433 | A | 9/1998 | Benzel et al. |
| 5,861,041 | A | 1/1999 | Tienboon |
| 5,865,845 | A | 2/1999 | Thalgott |
| 5,865,849 | A | 2/1999 | Stone |
| 5,876,402 | A | 3/1999 | Errico et al. |
| 5,876,452 | A | 3/1999 | Athanasiou et al. |
| 5,885,299 | A | 3/1999 | Winslow et al. |
| 5,888,222 | A | 3/1999 | Coates et al. |
| 5,888,223 | A | 3/1999 | Bray |
| 5,888,224 | A | 3/1999 | Beckers et al. |
| 5,888,227 | A | 3/1999 | Cottle |
| 5,895,426 | A | 4/1999 | Scarborough et al. |
| 5,899,939 | A | 5/1999 | Boyce et al. |
| 5,902,338 | A | 5/1999 | Stone |
| 5,904,719 | A | 5/1999 | Errico et al. |
| 5,910,315 | A | 6/1999 | Stevenson et al. |
| 5,922,027 | A | 7/1999 | Stone |
| 5,944,755 | A | 8/1999 | Stone |
| 5,954,722 | A | 9/1999 | Bono |
| 5,968,098 | A | 10/1999 | Winslow |
| 5,972,368 | A | 10/1999 | McKay |
| 5,976,187 | A | 11/1999 | Richelsoph |
| 5,980,522 | A | 11/1999 | Koros et al. |
| 5,981,828 | A | 11/1999 | Nelson et al. |
| 5,984,967 | A | 11/1999 | Zdeblick et al. |
| 5,989,289 | A | 11/1999 | Coates et al. |
| 6,013,853 | A | 1/2000 | Athanasiou et al. |
| 6,025,538 | A | 2/2000 | Yaccarino, III |
| 6,033,405 | A | 3/2000 | Winslow et al. |
| 6,033,438 | A | 3/2000 | Bianchi et al. |
| 6,039,762 | A | 3/2000 | McKay |
| 6,045,579 | A | 4/2000 | Hochshuler et al. |
| 6,045,580 | A | 4/2000 | Scarborough et al. |
| 6,056,749 | A | 5/2000 | Kuslich |
| 6,066,175 | A * | 5/2000 | Henderson et al. ........ 623/17.11 |
| 6,080,158 | A | 6/2000 | Lin |
| 6,080,193 | A | 6/2000 | Hochshuler et al. |
| 6,090,998 | A | 7/2000 | Grooms et al. |
| 6,096,080 | A | 8/2000 | Nicholson et al. |
| 6,096,081 | A | 8/2000 | Grivas et al. |
| 6,099,531 | A | 8/2000 | Bonutti |
| 6,110,482 | A | 8/2000 | Khouri et al. |
| 6,113,638 | A * | 9/2000 | Williams et al. ............... 128/898 |
| 6,120,503 | A | 9/2000 | Michelson |
| 6,123,731 | A | 9/2000 | Boyce et al. |
| 6,129,763 | A | 10/2000 | Chauvin et al. |
| 6,136,001 | A | 10/2000 | Michelson |
| 6,139,550 | A | 10/2000 | Michelson |
| 6,143,030 | A | 11/2000 | Schroder |
| 6,143,033 | A | 11/2000 | Paul et al. |
| 6,156,070 | A | 12/2000 | Incavo et al. |
| 6,193,721 | B1 | 2/2001 | Michelson |
| 6,193,756 | B1 | 2/2001 | Studer et al. |
| 6,200,347 | B1 | 3/2001 | Anderson et al. |
| 6,206,922 | B1 | 3/2001 | Zdeblick et al. |
| 6,224,602 | B1 * | 5/2001 | Hayes ............................ 606/296 |
| 6,231,610 | B1 | 5/2001 | Geisler |
| 6,235,033 | B1 | 5/2001 | Brace et al. |
| 6,235,034 | B1 | 5/2001 | Bray |
| 6,235,059 | B1 | 5/2001 | Benezech et al. |
| 6,241,769 | B1 | 6/2001 | Nicholson et al. |
| 6,245,108 | B1 | 6/2001 | Biscup |
| 6,258,089 | B1 | 7/2001 | Campbell et al. |
| 6,258,125 | B1 | 7/2001 | Paul et al. |
| 6,261,291 | B1 | 7/2001 | Talaber et al. |
| 6,261,586 | B1 | 7/2001 | McKay |
| 6,264,695 | B1 | 7/2001 | Stoy |
| 6,270,528 | B1 | 8/2001 | McKay |
| 6,306,139 | B1 | 10/2001 | Fuentes |
| 6,342,074 | B1 | 1/2002 | Simpson |
| 6,364,880 | B1 | 4/2002 | Michelson |
| 6,371,986 | B1 | 4/2002 | Bagby |
| 6,383,186 | B1 | 5/2002 | Michelson |
| 6,387,130 | B1 | 5/2002 | Stone et al. |
| 6,413,259 | B1 * | 7/2002 | Lyons et al. ................... 606/295 |
| 6,423,063 | B1 | 7/2002 | Bonutti |
| 6,432,106 | B1 * | 8/2002 | Fraser ......................... 623/17.11 |
| 6,447,512 | B1 | 9/2002 | Landry et al. |
| 6,447,546 | B1 | 9/2002 | Bramlet et al. |
| 6,454,771 | B1 | 9/2002 | Michelson |
| 6,458,158 | B1 | 10/2002 | Anderson et al. |
| 6,468,311 | B2 | 10/2002 | Boyd et al. |
| 6,471,724 | B2 | 10/2002 | Zdeblick et al. |
| 6,503,250 | B2 | 1/2003 | Paul |
| 6,524,312 | B2 | 2/2003 | Landry et al. |

(56) References Cited

U.S. PATENT DOCUMENTS

| | | | |
|---|---|---|---|
| 6,558,387 B2 | 5/2003 | Errico et al. | |
| 6,558,423 B1* | 5/2003 | Michelson | 623/17.11 |
| 6,562,073 B2 | 5/2003 | Foley | |
| 6,569,201 B2 | 5/2003 | Moumene et al. | |
| 6,575,975 B2 | 6/2003 | Brace et al. | |
| 6,576,017 B2 | 6/2003 | Foley et al. | |
| 6,605,090 B1 | 8/2003 | Trieu et al. | |
| 6,616,671 B2 | 9/2003 | Landry et al. | |
| 6,620,163 B1 | 9/2003 | Michelson | |
| 6,623,486 B1 | 9/2003 | Weaver et al. | |
| 6,629,998 B1 | 10/2003 | Lin | |
| 6,638,310 B2 | 10/2003 | Lin et al. | |
| 6,645,212 B2 | 11/2003 | Goldhahn et al. | |
| 6,656,181 B2 | 12/2003 | Dixon et al. | |
| 6,679,887 B2 | 1/2004 | Nicholson et al. | |
| 6,682,563 B2 | 1/2004 | Scharf | |
| 6,695,846 B2 | 2/2004 | Richelsoph et al. | |
| 6,695,851 B2 | 2/2004 | Zdeblick et al. | |
| 6,709,456 B2 | 3/2004 | Langberg et al. | |
| 6,712,818 B1 | 3/2004 | Michelson | |
| 6,730,127 B2 | 5/2004 | Michelson | |
| 6,736,850 B2 | 5/2004 | Davis | |
| 6,761,739 B2 | 7/2004 | Shepard | |
| 6,786,909 B1* | 9/2004 | Dransfeld et al. | 606/283 |
| 6,805,714 B2 | 10/2004 | Sutcliffe | |
| 6,808,537 B2 | 10/2004 | Michelson | |
| 6,824,564 B2 | 11/2004 | Crozet | |
| 6,837,905 B1 | 1/2005 | Lieberman | |
| 6,849,093 B2 | 2/2005 | Michelson | |
| 6,855,168 B2 | 2/2005 | Crozet | |
| 6,890,334 B2 | 5/2005 | Brace et al. | |
| 6,899,735 B2 | 5/2005 | Coates et al. | |
| 6,916,320 B2 | 7/2005 | Michelson | |
| 6,962,606 B2 | 11/2005 | Michelson | |
| 6,972,019 B2 | 12/2005 | Michelson | |
| 6,972,035 B2 | 12/2005 | Michelson | |
| 6,974,479 B2 | 12/2005 | Trieu | |
| 6,984,234 B2 | 1/2006 | Bray | |
| 7,001,385 B2 | 2/2006 | Bonutti | |
| 7,001,432 B2 | 2/2006 | Keller et al. | |
| 7,033,394 B2 | 4/2006 | Michelson | |
| 7,041,135 B2 | 5/2006 | Michelson | |
| 7,044,968 B1 | 5/2006 | Yaccarino et al. | |
| 7,060,097 B2 | 6/2006 | Fraser et al. | |
| 7,077,864 B2 | 7/2006 | Byrd, III et al. | |
| 7,112,222 B2 | 9/2006 | Fraser et al. | |
| 7,112,223 B2 | 9/2006 | Davis | |
| 7,135,024 B2 | 11/2006 | Cook et al. | |
| 7,135,043 B2 | 11/2006 | Nakahara et al. | |
| 7,137,984 B2 | 11/2006 | Michelson | |
| 7,147,665 B1 | 12/2006 | Bryan et al. | |
| 7,163,561 B2 | 1/2007 | Michelson | |
| 7,172,627 B2 | 2/2007 | Fiere et al. | |
| 7,232,463 B2 | 6/2007 | Falahee | |
| 7,232,464 B2 | 6/2007 | Mathieu et al. | |
| 7,255,698 B2 | 8/2007 | Michelson | |
| 7,276,082 B2 | 10/2007 | Zdeblick et al. | |
| 7,320,708 B1 | 1/2008 | Bernstein | |
| 7,323,011 B2 | 1/2008 | Shepard et al. | |
| 7,608,107 B2 | 10/2009 | Michelson | |
| 7,618,456 B2 | 11/2009 | Mathieu et al. | |
| 7,862,616 B2 | 1/2011 | Lechmann et al. | |
| 7,875,076 B2 | 1/2011 | Mathieu et al. | |
| 8,328,872 B2 | 12/2012 | Duffield et al. | |
| 8,343,222 B2 | 1/2013 | Cope | |
| 2001/0001129 A1 | 5/2001 | McKay et al. | |
| 2001/0005796 A1 | 6/2001 | Zdeblick et al. | |
| 2001/0010021 A1 | 7/2001 | Boyd et al. | |
| 2001/0016777 A1 | 8/2001 | Biscup | |
| 2001/0031254 A1 | 10/2001 | Bianchi et al. | |
| 2001/0039456 A1 | 11/2001 | Boyer, II et al. | |
| 2001/0041941 A1 | 11/2001 | Boyer, II et al. | |
| 2002/0004683 A1 | 1/2002 | Michelson et al. | |
| 2002/0010511 A1 | 1/2002 | Michelson | |
| 2002/0016595 A1 | 2/2002 | Michelson | |
| 2002/0022843 A1 | 2/2002 | Michelson | |
| 2002/0029084 A1 | 3/2002 | Paul et al. | |
| 2002/0065517 A1 | 5/2002 | Paul | |
| 2002/0082597 A1 | 6/2002 | Fraser | |
| 2002/0082603 A1 | 6/2002 | Dixon et al. | |
| 2002/0091447 A1 | 7/2002 | Shimp et al. | |
| 2002/0095155 A1 | 7/2002 | Michelson | |
| 2002/0099376 A1 | 7/2002 | Michelson | |
| 2002/0106393 A1 | 8/2002 | Bianchi et al. | |
| 2002/0111680 A1 | 8/2002 | Michelson | |
| 2002/0128712 A1 | 9/2002 | Michelson | |
| 2002/0128717 A1 | 9/2002 | Alfaro et al. | |
| 2002/0147450 A1* | 10/2002 | LeHuec et al. | 606/61 |
| 2002/0169508 A1 | 11/2002 | Songer et al. | |
| 2002/0193880 A1 | 12/2002 | Fraser | |
| 2003/0078668 A1 | 4/2003 | Michelson | |
| 2003/0125739 A1 | 7/2003 | Bagga et al. | |
| 2003/0135277 A1 | 7/2003 | Bryan et al. | |
| 2003/0153975 A1 | 8/2003 | Byrd | |
| 2003/0167092 A1 | 9/2003 | Foley | |
| 2003/0195626 A1 | 10/2003 | Huppert | |
| 2003/0195632 A1 | 10/2003 | Foley et al. | |
| 2004/0078078 A1* | 4/2004 | Shepard | 623/17.11 |
| 2004/0078081 A1 | 4/2004 | Ferree | |
| 2004/0093084 A1 | 5/2004 | Michelson | |
| 2004/0102848 A1 | 5/2004 | Michelson | |
| 2004/0176853 A1 | 9/2004 | Sennett et al. | |
| 2004/0199254 A1 | 10/2004 | Louis et al. | |
| 2004/0210310 A1 | 10/2004 | Trieu | |
| 2004/0210314 A1 | 10/2004 | Michelson | |
| 2004/0249377 A1 | 12/2004 | Kaes et al. | |
| 2004/0254644 A1 | 12/2004 | Taylor | |
| 2005/0015149 A1 | 1/2005 | Michelson | |
| 2005/0021143 A1 | 1/2005 | Keller | |
| 2005/0033433 A1 | 2/2005 | Michelson | |
| 2005/0049593 A1 | 3/2005 | Duong et al. | |
| 2005/0049595 A1 | 3/2005 | Suh et al. | |
| 2005/0065608 A1 | 3/2005 | Michelson | |
| 2005/0071008 A1 | 3/2005 | Kirschman | |
| 2005/0085913 A1 | 4/2005 | Fraser et al. | |
| 2005/0101960 A1 | 5/2005 | Fiere et al. | |
| 2005/0159813 A1 | 7/2005 | Molz | |
| 2005/0159819 A1 | 7/2005 | McCormick et al. | |
| 2005/0240271 A1 | 10/2005 | Zubock et al. | |
| 2006/0030851 A1 | 2/2006 | Bray et al. | |
| 2006/0079901 A1 | 4/2006 | Ryan et al. | |
| 2006/0079961 A1 | 4/2006 | Michelson | |
| 2006/0085071 A1 | 4/2006 | Lechmann et al. | |
| 2006/0129240 A1 | 6/2006 | Lessar et al. | |
| 2006/0136063 A1 | 6/2006 | Zeegers | |
| 2006/0142765 A9 | 6/2006 | Dixon et al. | |
| 2006/0195189 A1 | 8/2006 | Link et al. | |
| 2007/0088441 A1 | 4/2007 | Duggal et al. | |
| 2007/0123987 A1 | 5/2007 | Bernstein | |
| 2007/0162130 A1 | 7/2007 | Rashbaum et al. | |
| 2007/0168032 A1 | 7/2007 | Muhanna et al. | |
| 2007/0219635 A1 | 9/2007 | Mathieu et al. | |
| 2007/0225806 A1 | 9/2007 | Squires et al. | |
| 2007/0225812 A1 | 9/2007 | Gill | |
| 2007/0270961 A1 | 11/2007 | Ferguson | |
| 2008/0051890 A1 | 2/2008 | Waugh et al. | |
| 2008/0119933 A1 | 5/2008 | Aebi et al. | |
| 2008/0133013 A1 | 6/2008 | Duggal et al. | |
| 2008/0177307 A1 | 7/2008 | Moskowitz et al. | |
| 2008/0249569 A1 | 10/2008 | Waugh et al. | |
| 2008/0249575 A1 | 10/2008 | Waugh et al. | |
| 2008/0269806 A1 | 10/2008 | Zhang et al. | |
| 2008/0306596 A1 | 12/2008 | Jones et al. | |
| 2009/0076608 A1 | 3/2009 | Gordon et al. | |
| 2009/0105830 A1 | 4/2009 | Jones et al. | |
| 2010/0016901 A1 | 1/2010 | Robinson | |

FOREIGN PATENT DOCUMENTS

| | | |
|---|---|---|
| DE | 39 33 459 A1 | 4/1991 |
| DE | 42 42 889 A1 | 6/1994 |
| DE | 44 09 392 A1 | 9/1995 |
| DE | 4423257 | 1/1996 |
| DE | 195 04 867 C1 | 2/1996 |

(56) References Cited

FOREIGN PATENT DOCUMENTS

| | | |
|---|---|---|
| DE | 299 13 200 U1 | 9/1999 |
| EP | 0505634 A1 | 9/1992 |
| EP | 0517030 A2 | 12/1992 |
| EP | 0517030 A3 | 4/1993 |
| EP | 0577178 A1 | 1/1994 |
| EP | 0639351 A2 | 2/1995 |
| EP | 0639351 A3 | 3/1995 |
| EP | 0517030 B1 | 9/1996 |
| EP | 0505634 B1 | 8/1997 |
| EP | 0966930 | 12/1999 |
| EP | 0 974 319 A2 | 1/2000 |
| EP | 0968692 A1 | 1/2000 |
| EP | 0974319 | 1/2000 |
| EP | 1033941 | 9/2000 |
| EP | 1051133 | 11/2000 |
| EP | 1103236 | 5/2001 |
| EP | 0906065 B1 | 1/2004 |
| FR | 2552659 | 4/1985 |
| FR | 2 697 996 | 5/1994 |
| FR | 2 700 947 | 8/1994 |
| FR | 2727003 | 5/1996 |
| FR | 2 747 034 A1 | 10/1997 |
| FR | 2 753 368 | 3/1998 |
| GB | 2 148 122 A | 5/1985 |
| GB | 2148122 | 5/1985 |
| GB | 2207607 | 2/1989 |
| SU | 1465040 A1 | 3/1989 |
| WO | WO 88/03417 | 5/1988 |
| WO | WO 88/10100 | 12/1988 |
| WO | WO 92/01428 | 2/1992 |
| WO | WO 95/21053 | 8/1995 |
| WO | WO 96/39988 | 12/1996 |
| WO | WO 97/20526 | 6/1997 |
| WO | WO 97/25941 | 7/1997 |
| WO | WO 97/25945 | 7/1997 |
| WO | WO 97/39693 | 10/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/27864 | 6/1999 |
| WO | WO 99/29271 | 6/1999 |
| WO | WO 99/63914 | 6/1999 |
| WO | WO 99/32055 | 7/1999 |
| WO | WO 99/38461 | 8/1999 |
| WO | WO 99/38463 | 8/1999 |
| WO | WO 99/38463 A2 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 A | 11/2000 |
| WO | WO 00/66045 A1 | 11/2000 |
| WO | WO 00/74607 A1 | 12/2000 |
| WO | WO 01/08611 | 2/2001 |
| WO | WO 01/56497 A2 | 8/2001 |
| WO | WO 01/62190 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 A1 | 12/2001 |
| WO | WO 01/93742 A3 | 9/2002 |
| WO | WO 2007/098288 | 8/2007 |
| WO | WO 2009/064644 | 5/2009 |

OTHER PUBLICATIONS

U.S. Appl. No. 11/199,599: Appeal Brief, dated Apr. 15, 2010, 51 pages.
U.S. Appl. No. 11/199,599: Final Rejection, dated Dec. 24, 2009, 21 pages.
U.S. Appl. No. 11/199,599: Interview Summary included Draft Amendments, dated Sep. 24, 2009, 16 pages.
U.S. Appl. No. 11/199,599: Non-Final Rejection, dated Apr. 1, 2009, 20 pages.
U.S. Appl. No. 11/199,599: Preliminary Amendment, dated Jan. 9, 2008, 11 pages.
"Jury Trial Demanded", In the United States District Court for the District of Delaware, Case No. 1:11-cv-00652-LPS, filed Jul. 22, 2011, 8 pages.
Chadwick et al., "Radiolucent Structural Materials for Medical Applications," www.mddionline.com/print/238, Jun. 1, 2001, accsessed date Jul. 31, 2012, 9 pages.
Jonbergen et al., "Anterior Cervical Interbody fusion with a titanium box cage: Early radiological assessment of fusion and subsidence", The Spine Journal 5, Jul. 2005, 645-649.
Marcolongo et al., "Trends in Materials for Spine Surgery", Biomaterials and Clinical Use, 6, 2011, 21 pages.
Parlov et al., Anterior Lumbar Interbody Fusion with Threaded Fusion Cages and Autologous Grafts, Eur. Spine J., 2000, 9, 224-229.
Schleicher et al., "Biomechanical Comparison of Two Different Concepts for Stand alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Spruit et al., The in Vitro Stabilising Effect of Polyether-etherketone Cages Versus a Titanium Cage of similar design for anterior lumbar interbody fusion, Eur. Spine J., Aug. 2005, 14 752-758.
"Expert Report of Paul Ducheyne, Ph.D. Concerning Patent Validity", United States District Court District of Delaware, Civil Action No. 1:11-cv-00652-LPS, Dec. 13, 2012, 155 pages.
"Expert Report of Richard J. Gering, Ph.D., CLP" In the United States District Court for the District of Delaware, Civil Action No. 1:11-cv-00652-LPS, Dec. 14, 2012, 39 pages.
"Expert Report of John F. Hall, M.D.", United States District Court for the District of Delaware, Civil Action No. 1:11-cv-00652-LPS, Dec. 14, 2012, 27 pages.
"Second Expert Report of Wilson C. Hayes, Ph.D.", United States District Court for the District of Delaware, Civil Action No. 1:11-cv-00652-LPS, Dec. 14, 2012, 22 pages.
"Expert Report of Dr. Domagoj Coric Regarding the Invalidity of U.S. Patent No. 7,846,207, 7,862,616 and 7,875,076", In the United States District Court for the District of Delaware, Civil Action No. 1:11-cv-00652-LPS, Nov. 5, 2012, 149 pages.
"Reply Report of Dr. Domagoj Coric Regarding the Invalidity of U.S. Patent Nos. 7,846,207, 7,862,616 and 7,875,076", in the United States District Court for the District of Delaware, Civil Action No. 1:11-cv-00652-LPS, Jan. 4, 2013, 81 pages.
"Joint Claim Construction Brief", In the United States District Court for the District of Delaware, Civil Action No. 1:11-cv-00652-LPS, Jun. 14, 2012, 97 pages.
"Plaintiffs' Responses and Objections to Defendant Globus Medical, Inc.'s First Set of Interrogatories (Nos. 1-11)", United States District Court for the District of Delaware, Civil Action No. 1:11-cv-00652-LPS, Nov. 14, 2011, 18 pages.
"Plaintiffs' Supplemental Responses and Objections to Defendant Globus Medical Inc.'s Interrogatories No. 6-10 and Second Supplemental Responses and Objections to Interrogatory No. 5", United States District Court for the District of Delaware, Civil Action No. 11-cv-652-LPS, Sep. 1, 2012, 12 pages.
"Appendix 1 to Joint Claim Construction Brief; Synthes' Exhibits A-9", In the United States District Court for the District of Delaware Civil Action No. 1:11-cv-00652-LPS, Jun. 8, 2012, 192 pages.
"Appendix 2 to Joint Claim Construction Brief; Globus' Exhibits A-F", In the United States District Court for the District of Delaware Civil Action No. 1:11-cv-00652-LPS, Jun. 8, 2012, 146 pages.
"Appendix 3 to Joint Claim Construction Brief; Exhibits A-C", In the United States District Court for the District of Delaware Civil Action No. 1:11-cv-00652-LPS, Jun. 8, 2012, 38 pages.
Trial Transcript, United States District Court District of Delaware, Civil Action No. 1:11-cv00652-LPS, Jun. 3, 2013, 98 pages.

(56) References Cited

OTHER PUBLICATIONS

Trial Transcript, United States District Court District of Delaware, Civil Action No. 1:11-cv00652-LPS, Jun. 4, 2013, 110 pages.
Trial Transcript, United States District Court District of Delaware, Civil Action No. 1:11-cv00652-LPS, Jun. 5, 2013, 99 pages.
Trial Transcript, United States District Court District of Delaware, Civil Action No. 1:11-cv00652-LPS, Jun. 6, 2013, 80 pages.
Trial Transcript, United States District Court District of Delaware, Civil Action No. 1:11-cv00652-LPS, Jun. 7, 2013, 97 pages.
Trial Transcript, United States District Court District of Delaware, Civil Action No. 1:11-cv00652-LPS, Jun. 10, 2013, 114 pages.
Trial Transcript, United States District Court District of Delaware, Civil Action No. 1:11-cv00652-LPS, Jun. 11, 2013, 98 pages.
Trial Transcript, United States District Court District of Delaware, Civil Action No. 1:11-cv00652-LPS, Jun. 12, 2013, 75 pages.
Trial Transcript, United States District Court District of Delaware, Civil Action No. 1:11-cv00652-LPS, Jun. 13, 2013, 94 pages.
Trial Transcript, United States District Court District of Delaware, Civil Action No. 1:11-cv00652-LPS, Jun. 14, 2013, 26 pages.
Jury Verdict Form, United States District Court District of Delaware, Civil Action No. 1:11-cv-00652-LPS, Jun. 14, 2013, 20 pages.
"Memorandum Opinion" United States District Court District of Delaware, Civil Action No. 1:11-cv-00652-LPS, May 7, 2013, 33 pages.
"Order" United States District Court District of Delaware, Civil Action No. 1:11-cv-00652-LPS, May 7, 2013, 7 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Plaintiff's Reply Brief in Support of Plaintiff's Motion for Summary Judgment of No Anticipation by the Kozak and Michelson References", Mar. 21, 2013, 11 pages.
"Order" United States District Court District of Delaware, Civil Action No. 1:11-cv-00652-LPS, May 15, 2013, 4 pages.

* cited by examiner

INTERVERTEBRAL IMPLANT

CROSS REFERENCE TO RELATED APPLICATION

This application is a continuation of U.S. patent application Ser. No. 12/432,088, filed on Apr. 29, 2009, now U.S. Pat. No. 7,862,616, issued on Jan. 4, 2011, entitled "INTERVERTEBRAL IMPLANT", which is a continuation of U.S. patent application Ser. No. 11/199,599, filed on Aug. 8, 2005, now U.S. Pat. No. 7,846,207, issued on Dec. 7, 2010, which is a continuation of International Patent Application No. PCT/CH2003/000089, filed Feb. 6, 2003. The entire disclosure of U.S. Pat. No. 7,862,616 and International Patent Application No. PCT/CH2003/000089 are incorporated herein by reference.

TECHNICAL FIELD

The present invention relates generally to intervertebral implants.

BACKGROUND OF THE INVENTION

GB-A-2 207 607 discloses an intervertebral implant, which has a horseshoe-shaped configuration with a plurality of cylindrical holes. The holes are smooth on the inside and only have a stop for the heads of the bone screws, which are to be introduced therein. A disadvantage of this arrangement is that the fastening screws, introduced therein, can be anchored only with their shaft in the bone. This does not result in a rigid connection with the horseshoe-shaped intervertebral implant. When the anchoring of the screw shaft in the bone is weakened, the intervertebral implant becomes movable with respect to the screw and the bone screws tend to migrate, endangering the blood vessels. Moreover, the loosening of the intervertebral implant can lead to a pseudoarthrosis.

U.S. Patent Publication US-A 2000/0010511 (Michelson) discloses an intervertebral implant, which, at its front surface, has two boreholes with an internal thread, into which bone screws with a threaded head can be introduced. A disadvantage of this implant is that the bone screws can become loose and are not secured against being screwed out or falling out. A further disadvantage is that the bone screws are fastened completely to the implant body itself and that therefore the latter experiences a relatively large stress.

Screws which emerge at the anterior or anterolateral edge of the vertebral body because of loosening run the risk of injuring main vessels such as the aorta and Vena calva, as well as supply vessels such as lumbar arteries and veins. Injury to these main vessels may result in internal bleeding possibly causing death within a very short time. Loosening of screws is more likely when they are not mounted angularly firmly.

SUMMARY OF THE INVENTION

The present invention is to provide a remedy for the above-discussed disadvantages. The present invention is directed to an intervertebral implant which can enter into a permanent, rigid connection with bone fixation means, so that, even if the bone structure is weakened, there is no loosening between the intervertebral implant and the bone fixation means. Moreover, over a separately constructed front plate, there is tension chording for the bone fixation elements, so that the implant body experiences less stress, that is, superimposed tensions. Moreover, a securing plate enables all bone fixation elements to be secured simultaneously.

The present invention accomplishes the objective set out above with an intervertebral implant, comprising a three-dimensional body having an upper side and an under side which are suitable for abutting the end plates of two adjacent vertebral bodies. The three-dimensional body further includes a left side surface and a right side surface, a front surface and a rear surface, a horizontal middle plane between the upper side and the under side, and a vertical middle plane extending from the front surface to the rear surface. The three-dimensional body further comprising a plurality of boreholes, having openings at least at or near the front surface, passing there through and being suitable for accommodating longitudinal fixation elements. The intervertebral implant further including a front plate displaceably disposed as an insert with the front side of the three-dimensional body, where the front plate includes a plurality of boreholes having openings and in which the longitudinal fixation elements can be anchored, and whose openings overlap with the openings of the boreholes of the three-dimensional body. The intervertebral implant has a securing plate fastened substantially parallel to the front plate in such a manner that the boreholes of the front plate are covered at least partly by the securing plate. An advantage achieved by the present invention, arises essentially from the solid connection between the intervertebral implant and the longitudinal fixation elements, used to fasten it.

Compared to the two-part implants of the state of the art, for which a front plate is implanted in a separate step, the present invention has the advantage that the implantation of the intervertebral implant may be carried out in one step and, with that, can be carried out more easily and more quickly. A further advantage is that the intervertebral implant is fixed as frontally as possible at the body of the vertebra. That is, at a place where good bone material usually is present. The result is an anterior movement limitation without a greater risk to the surrounding structures. The load is still absorbed under compression by the intervertebral implant and not by the front plate or the fixation screws (longitudinal fixation elements).

A method for implanting an intervertebral implant of the present invention between two adjacent vertebral bodies includes introducing the intervertebral implant, having a three-dimensional body, a front plate, and one or more boreholes, between two adjacent vertebral bodies, attaching longitudinal fixation elements with heads through the boreholes into the vertebral bodies, and attaching a securing plate by means of a fastening agent over the heads of the longitudinal fixation elements to the front plate, such that the heads of the longitudinal fixation elements are captured between the front plate and the securing plate wherein the longitudinal fixation elements are secured against being shifted relative to the intervertebral implant.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

DESCRIPTION OF THE PREFERRED EMBODIMENTS

Figure 1:
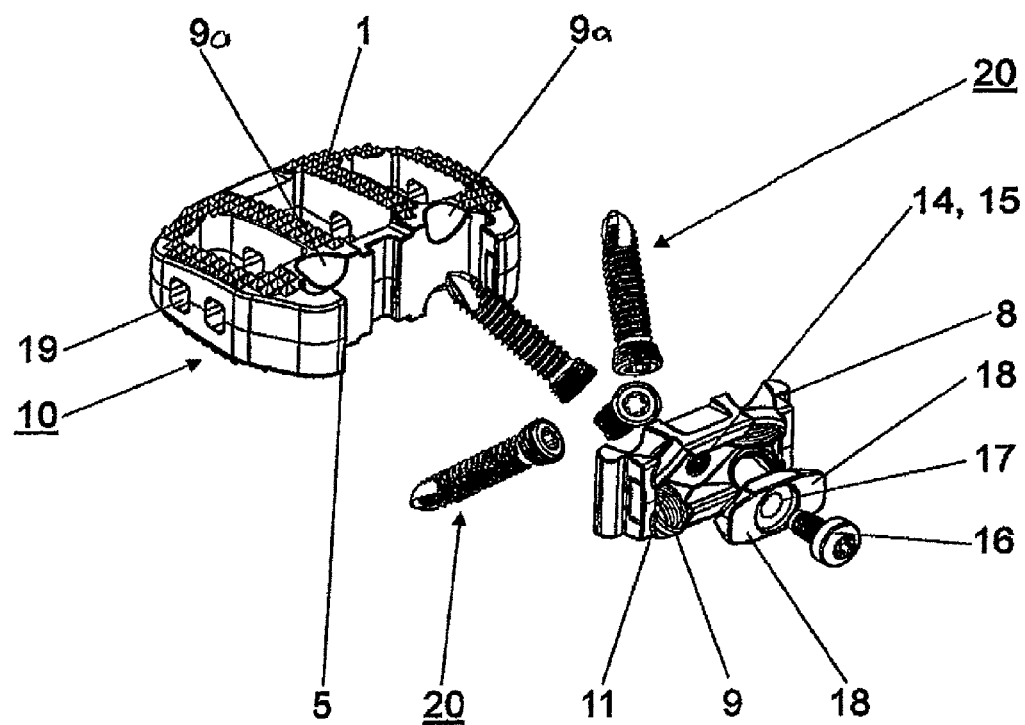
FIG. 1 shows an exploded drawing of the intervertebral implant.

The intervertebral implant, shown in FIG. 1-7, includes a three-dimensional body 10 in the form of a cage with an upper side 1 and an underside 2, which are suitable for abutting the end plates of two adjacent vertebral bodies, a left side surface 3 and a right side surface 4, a front surface 5 and a back surface 6, a horizontal middle plane 7 located between the upper side 1 and the underside 2, a vertical middle plane 12 extending from the front surface 5 to the rear surface 6 and four boreholes 9a, which pass through the body 10 and are suitable for accommodating longitudinal fixation elements 20. The body 10 may be constructed as a hollow body, the mantle surfaces of which are provided with perforations 19. The upper side 1 and/or under side 2 of the intervertebral implant may preferably be convex in shape, not planar. A convex shape to the upper side 1 and the underside 2 allows for an improved fit with the end plates of the adjacent vertebral bodies by the intervertebral implant. Further, the side surfaces 1-6 of the intervertebral implant may be essentially convex, as well.

Figure 7:
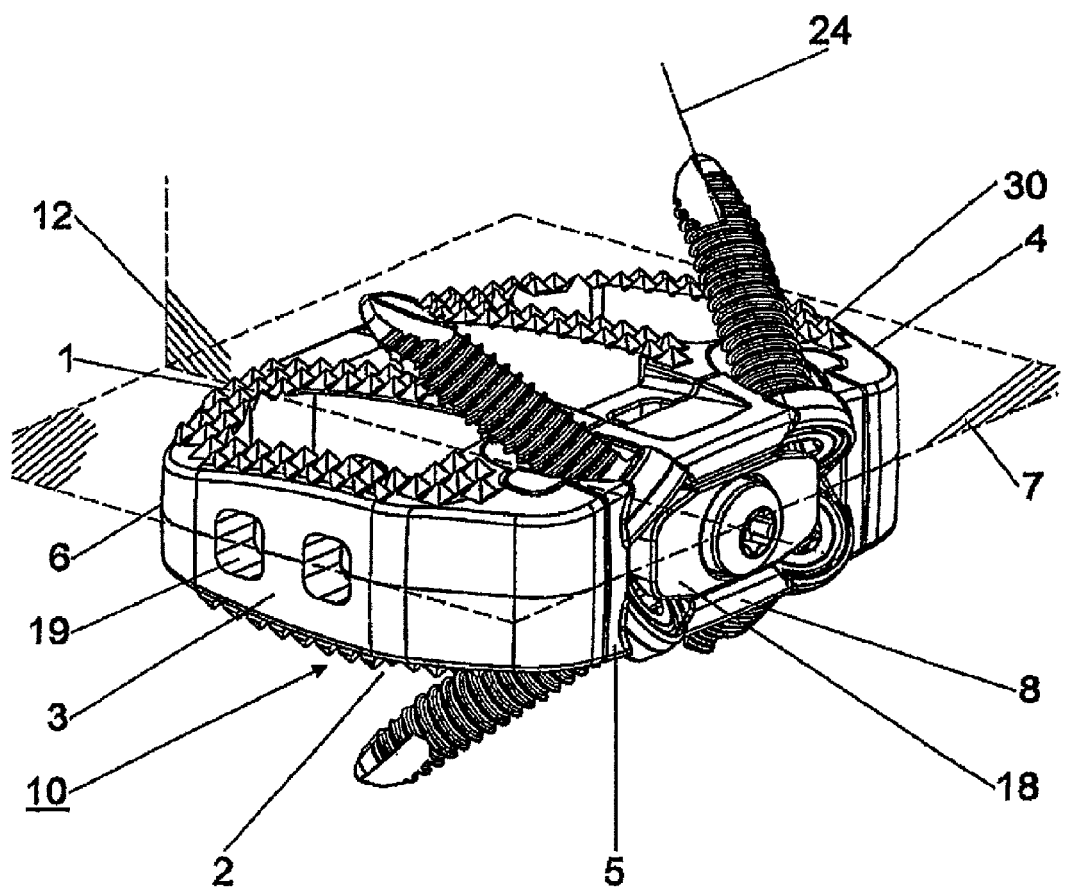
FIG. 7 shows a completely installed intervertebral implant with front plate and securing plate.

As shown in FIG. 7, the upper side 1 and the underside 2 of the three-dimensional body 10 are provided with structuring in the form of teeth 30.

Figures 5, 6:
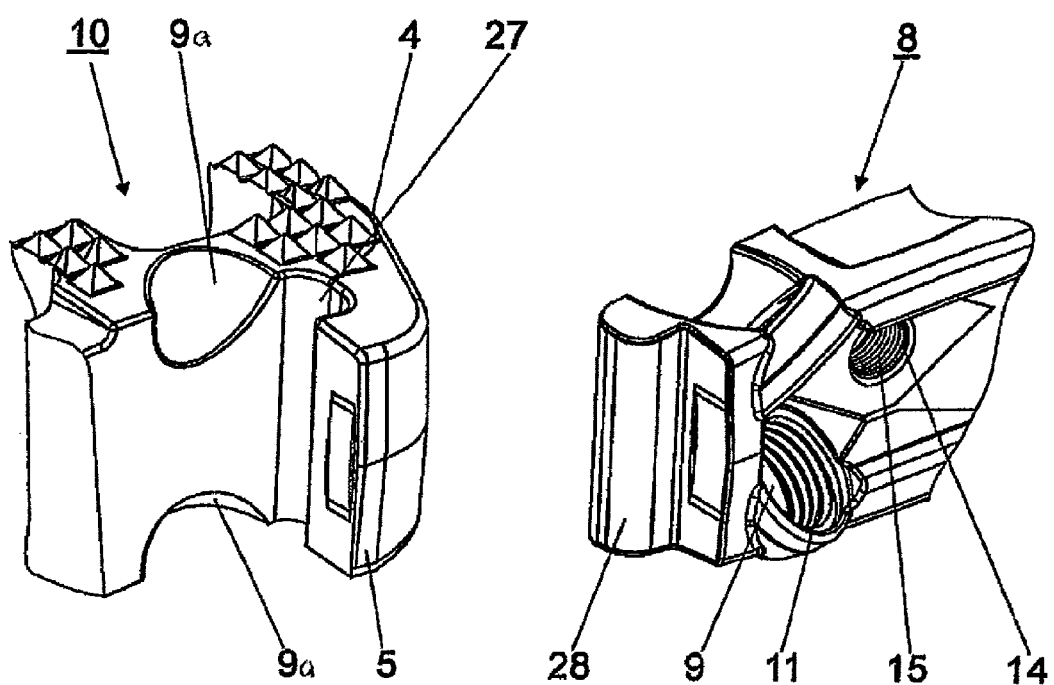
FIG. 5 shows a three-dimensional detailed representation of the body of the intervertebral implant, which shows the connecting elements to the front plate of FIG. 6.
FIG. 6 shows a three-dimensional detailed representation of the front plate of the intervertebral implant and the connecting elements to the body of FIG. 5

At the front surface of the three-dimensional body 10, a front plate 8 may be mounted, which is disposed perpendicular to the horizontal central plane of the intervertebral implant and through which four boreholes 9 pass and in which the longitudinal fixation elements 20 can be anchored. The front plate 8, as shown in FIGS. 5 and 6, is constructed as an insert for the three-dimensional body 10. The three-dimensional body 10 has a semicircular groove 27 extending parallel to the vertical middle plane 12 at the transitions of the left side surface 3 and the right side surface 4 (FIG. 5) to the front surface 5. Correspondingly, the front plate 8 has right and left (FIG. 6) similarly extending and similarly dimensioned, semicircular rail 28. As a result, the front plate can be pushed and positioned easily with its two lateral rails 28 into the corresponding grooves 27 of the body 10 during the production of the intervertebral implant.

In one embodiment, at least one of the boreholes 9 in the front plate is constructed so that a longitudinal fixation element 20, accommodated therein, can be connected rigidly with the front plate. A rigid connection may be accomplished, for example, owing to the fact that at least one of the boreholes 9 of the front plate 8 has an internal thread. A corresponding longitudinal fixation element 20, bone screw, with a threaded end can then be screwed together rigidly with the implant. In an alternative embodiment, the four boreholes 9 in the front plate may have an internal thread 11, so that longitudinal fixation elements 20 can be connected rigidly with the front plate 8.

As discussed, the front plate 8 may be disposed, preferably vertically to the horizontal central plane, so that it can be displaced vertically with respect to the three-dimensional body 10. By these means, "stress shielding" (protection and neutralization of mechanical stresses) is attained, which permits the end plates to be adapted to the intervertebral implant during the healing process.

The intervertebral implant may have a securing plate 18, which can be fastened by means of a screw connection parallel to the front plate 8 at the front plate 8 in such a manner that the boreholes 9 of the front plate 8 are partly covered by the securing plate 18. The securing plate 18 may have a central borehole 17 provided, preferably, with an internal thread. Corresponding thereto, the front plate 8 has a central borehole 15 for accommodating fastening means 16. Preferably, the central borehole 15 has an internal thread 14 for accommodating a fastening means 16 in the form of a screw. The securing plate 18 may also be fastened by a bayonet catch or a click catch. By fastening the securing plate 18 to the front plate 8, the heads 21 of the longitudinal fixation elements 20 (discussed later) are contacted by the securing plate 18, so that they are secured against being ejected or screwed out.

Figure 3:
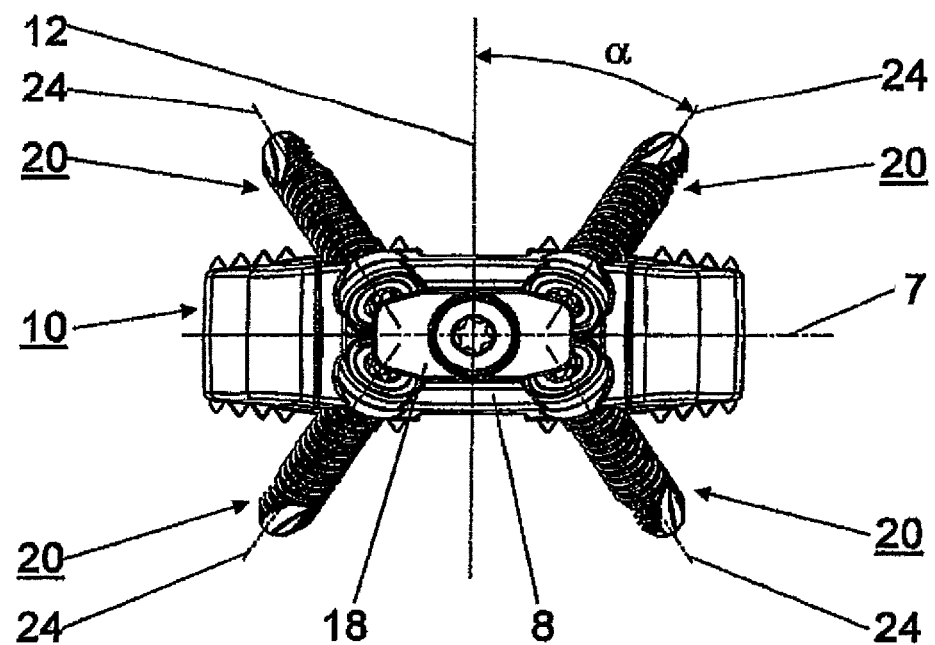
FIG. 3 shows an elevation of the intervertebral implant of FIG. 1.
Figure 4:
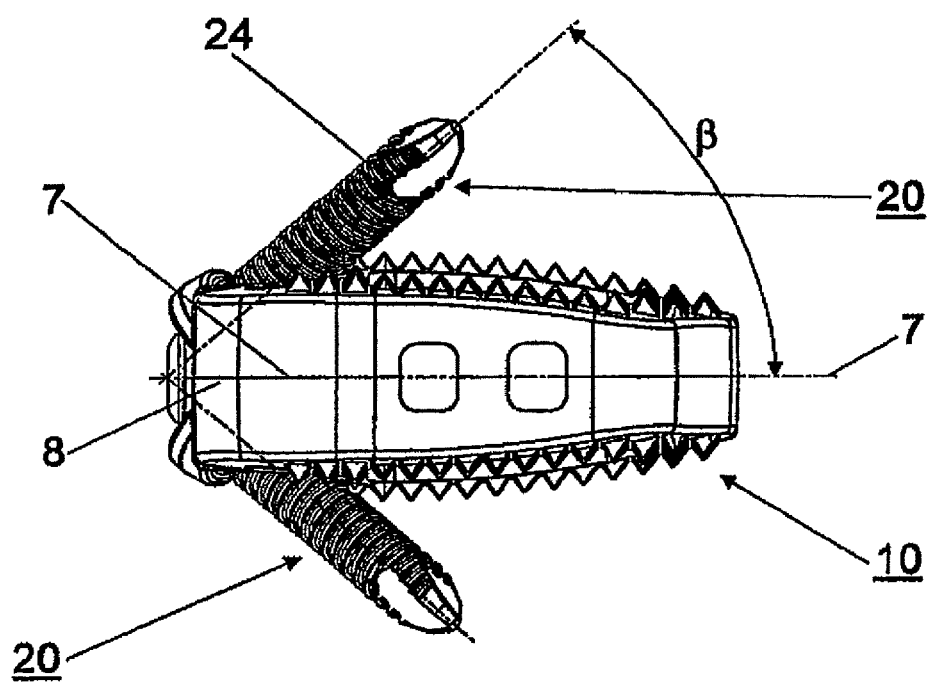
FIG. 4 shows a side view of the intervertebral implant of FIG. 1.

Preferably, the boreholes 9a of the three-dimensional body 10 do not pass either through the left side surface 3 or the right side surface 4 or completely through the front surface 5. The front surface 5, preferably, is also not crossed by the boreholes 9a. Further, the horizontal middle plane 7 is not pierced by the boreholes 9a. Only the axes 24 of the longitudinal fixation elements 20, introduced therein, intersect the horizontal middle plane 7 of the body 10. As seen from the front surface 5, the boreholes of the three-dimensional body 10 and the front plate diverge. The axes 24 of the boreholes of the three-dimensional plate 10 and the front plate 8 enclose an angle β ranging from 20° to 60°, specifically from 36° to 48°, and more preferably an angle β of 42° with the horizontal middle plane 7 (FIG. 4) and an angle α ranging from 10° to 45°, specifically from 27° to 33°, and more preferably an angle α of 30° with the vertical middle plane 12 (FIG. 3). Thus, better access for introducing the screws is achieved.

In one embodiment, at least one of the boreholes 9 of the front plate 8 may taper conically towards the underside 2, so that a bone screw, with a corresponding conical head, can be anchored rigidly therein. The conical borehole preferably has a conical angle, which is smaller than the resulting frictional angle. Advisably, the conicity of the conical borehole is 1:3.75 to 1:20.00 and preferably 1:5 to 1:15.

In another configuration, at least two of the boreholes 9 of the front plate 8 extend parallel to each other. This makes insertion of the intervertebral implant easier. In another embodiment, at least two of the boreholes 9 of the front plate 8 diverge when viewed from the front side. By these means, a region of the vertebral body, which has a better bone quality than does the center of the vertebral body, is reached by the bone screws.

To improve the anchoring of the bone screw in a plastic body of the intervertebral implant (discussed later), a metal sleeve with an internal thread (not shown) may be inserted in the boreholes of the front plate and three-dimensional body. The intervertebral implant may also consist only partially of an x-ray transparent plastic and, in the region of the boreholes consist of a metal, such as titanium or a titanium alloy. Improved guidance and anchoring of the bone screws in the intervertebral implant may be achieved. Further, the boreholes 9 may have a smooth internal wall, into which the threaded head of a metallic, longitudinal fixation element may cut or be molded.

Depending on circumstances, two, three, four or more longitudinal fixation elements may be connected rigidly with the intervertebral implant. Preferably, at least one fixation element should pierce the upper side and at least one fixation element the underside of the intervertebral implant. The longitudinal fixation elements 20 may have either a smooth head, so that there will not be a rigid connection with the implant or a threaded, conical or expendable end, so that there will be a rigid connection with the implant. In both cases, however, the longitudinal fixation elements 20 are secured by the securing plate against rotating out, being ejected out or falling out at a later time.

Figure 2:
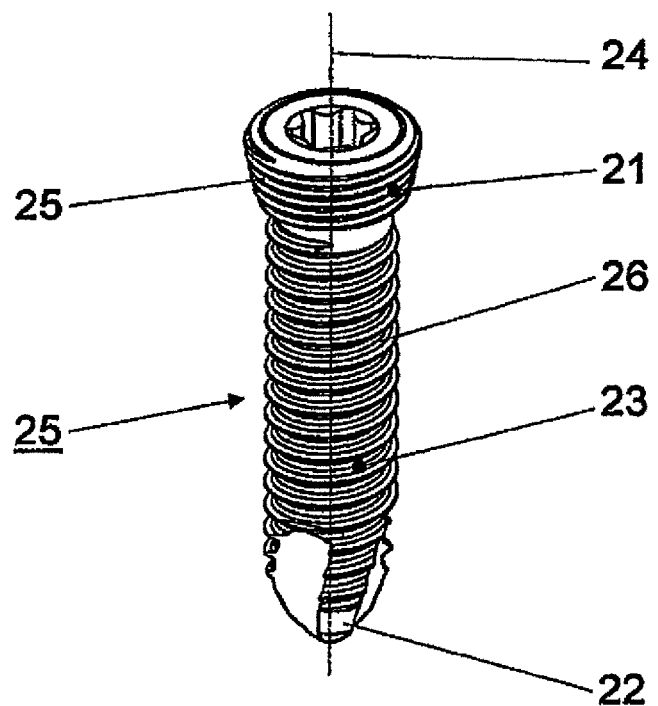
FIG. 2 shows a longitudinal fixation element in the form of a screw.

The longitudinal fixation elements 20 are preferably constructed as bone screws. As shown in FIG. 2, the longitudinal fixation elements 20, introduced into the boreholes 9, have a head 21, a tip 22, a shaft 23 and an axis 24. The head 21 may preferably be provided with an external thread 25, which corresponds to the internal thread 11 of the borehole 9, so that the heads 21 can be anchored in the boreholes 9 in a rigid manner. The shaft 23 may be provided with a thread 26, which is self-drilling and self-cutting. The load thread angle of the thread 26 has a range of between 11° to 14°, preferably between 12° and 13°, and more preferably a load thread angle of 115°. The pitch angle of the thread may have a range of between 6° and 10°, preferably between 7° and 9°, and more preferably have a pitch angle of 8°. The special pitch angle produces a self-retardation in the thread, thus ensuring that the bone screw will not automatically become loose.

In the case of a second, possibly rigid type of connection, a longitudinal fixation element 20, bone screw, may preferably be used, the head of which tapers conically towards the shaft, the conicity of the head corresponding to the conicity of the borehole of the intervertebral implant. The longitudinal fixation elements may also be constructed as threadless cylindrical pins, which are provided with a drilling tip, preferably in the form of a trocar. A further variation consist therein that the longitudinal fixation elements are constructed as spiral springs. Finally, the longitudinal fixation elements may also be constructed as single-vaned or multi-vaned spiral blades.

As shown in FIG. 7, two longitudinal fixation elements 20 pierce the upper side 1 and two longitudinal fixation elements 20 pierce the underside 2 of the body 10, thereby anchoring the intervertebral implant to the adjacent vertebral bodies.

The intervertebral implant may be produced from any material which is compatible with the body. Preferably, the three-dimensional body 10 may consist of a body-compatible plastic which has not been reinforced and which may be transparent to x-rays. The advantage over fiber-reinforced plastics, which are already known in implant technology, is that no reinforcing fibers are exposed. Such exposure may be disadvantageous clinically. In such a three-dimensional body 10 constructed of a plastic that has not been reinforced, the use bone screws may be preferable. As discussed previously, the external thread of the bone screw(s) may have a load thread angle range of 11° to 14°, and preferably between 12° to 13°. A comparatively slight inclination of the load flank brings about a high clamping force. As a result, radial expansion and the danger of forming cracks in the plastic are reduced. Furthermore, the external thread of the bone screw(s) may preferably have a pitch angle between 6° and 10° and preferably between 7° and 9°.

The front plate 8 may be made from materials different than the three-dimensional body 10. The front plate 8 is preferably made from a metallic material. Titanium or titanium alloys are particularly suitable as metallic materials. The complete tension chord arrangement (front plate and screws) may also be made from implant steel or highly alloyed metallic materials, such as CoCrMo or CoCrMoC. The advantage of titanium lies in that there is good tissue compatibility and the good ingrowing behavior of bones. The advantage of highly alloyed metallic materials lies in their high-strength values, which permit filigree constructions.

A brief description of a surgical procedure follows in order to explain the invention further.

The intervertebral implant, in the form of a three-dimensional body 10, is introduced between two adjacent vertebral bodies by means of a suitable instrument. Longitudinal fixation elements 20, in the form of bone screws, securing the three-dimensional body 10 are screwed/inserted by means of a suitable aiming device through the boreholes 9 of the front plate 8 into the vertebral bodies. The front plate 8 may be displaced vertically with respect to the three-dimensional body 10, such that the openings of the boreholes 9a of the three-dimensional plate 10 and the boreholes 9 of the front plate 8 overlap, to obtain stress shielding. The securing plate 18 is fastened by means of the fastening agent 16 in the form of a screw over the heads 21 of the longitudinal fixation elements 20 at the front plate 8, so that the heads 21 of the longitudinal fixation elements 20 and, with that, the screws themselves, are captured between the front plate 8 and the securing plate 18 and secured against being shifted relative to the three-dimensional body 10 (for example, by falling out or by turning out). The fastening agent 16, in the form of a screw, preferably is provided with a thread, which is distinguished by a large self-retardation.

The invention claimed is:

1. A bone stabilizing system configured to be inserted into an intervertebral space, the bone stabilizing system comprising:
   (a) a plurality of bone screws each having a shaft and a head that is connected to the shaft, each of the shafts being elongate along a respective longitudinal central axis;
   (b) an integral one-piece body defining a front body surface, a rear body surface opposite the front body surface, a left side surface, a right side surface opposite the left side surface along a lateral direction, a lower body surface, an upper body surface spaced from the lower body surface in a first direction, a portion of the one-piece body that is continuous along the lateral direction from the left side surface to the right side surface, and a recess that extends at least into the upper body surface such that the recess defines a body opening that is open to the first direction,
   wherein the one-piece body is configured such that when the bone stabilizing system is inserted into the intervertebral space: 1) the upper body surface contacts an endplate of a first vertebra; and 2) the lower body surface contacts an endplate of a second vertebra;
   (c) a front plate configured to be mounted to the one-piece body, the front plate comprising a biocompatible, non-bone material, the front plate defining a front plate surface, a rear plate surface opposite the front plate surface such that when the front plate is mounted to the one-piece body the rear plate surface faces the front body surface, the front plate further defining a plurality of screw holes each configured to receive one of the plurality of bone screws such that the shaft of the respective one of the plurality of bone screws passes through the endplate of the first vertebra or the endplate of the second vertebra, wherein a first of the plurality of screw holes defines a first central axis that extends through a first opening and a second opening in the front plate such that the first central axis is at a first oblique angle relative to the rear plate surface, a second of the plurality of screw holes defines a second central axis that extends through a third opening and a fourth opening in the front plate such that the second central axis is at a second oblique angle relative to the rear plate surface, and when the front plate is mounted to the one-piece body: 1) the first opening is positioned in the front plate surface between the left side surface and the right side surface with respect to the lateral direction; 2) the third opening is positioned between the left side surface and the right side surface with respect to the lateral direction; and 3) the front plate is devoid of screw holes with an opening that A) is positioned in the front plate surface and B) has a center that is positioned beyond the body opening with respect to the first direction.

2. The system of claim 1, wherein the body opening is a first body opening, the lower body surface is spaced from the upper body surface in a second direction, the lower body surface defines a second opening that faces the second direction, and the front plate is devoid of screw holes positioned beyond the second opening with respect to the second direction when the front plate is mounted to the one-piece body.

3. The system of claim 1, wherein the front plate defines an uppermost plate surface and an opposed lowermost plate surface, at least a portion of both the uppermost and lowermost plate surfaces are configured to be disposed within the intervertebral space when the front plate is mounted to the one-piece body and the one-piece body is disposed within the intervertebral space.

4. The system of claim 3, wherein an entirety of the uppermost plate surface is configured to be disposed between the endplates of the first and second vertebrae when the front plate is mounted to the one-piece body and the one-piece body is disposed between the endplates of the first and second vertebrae.

5. The system of claim 3, wherein each of the first and second oblique angles is from about 30° to about 70°.

6. The system of claim 5, wherein the front plate and at least one of the screw holes in the front plate are configured such that a first of the plurality of bone screws inserted into a respective one of the plurality of screw holes pierces either the upper body surface or the lower body surface when the front plate is mounted to the one-piece body.

7. The system of claim 6, wherein the front plate is configured such that the first of the plurality of bone screws pierces the upper body surface and a second of the plurality of bone screws inserted into a respective one of the plurality of screw holes pierces the lower body surface when the front plate is mounted to the one-piece body.

8. The system of claim 5, wherein the first central axis extends toward the upper body surface when the front plate is mounted to the one-piece body and the second central axis extends toward the lower body surface when the front plate is mounted to the one-piece body.

9. The system of claim 5, wherein the front plate is formed of a metallic material and the one-piece body is formed from a non-metallic material.

10. The system of claim 9, wherein the one-piece body is made from a plastic material.

11. The system of claim 5, wherein the front plate defines a maximum plate height from the uppermost plate surface to the lowermost plate surface and wherein the front body surface defines a maximum body height from the upper body surface to the lower body surface that is substantially equal to the maximum plate height.

12. The system of claim 5, wherein the front body surface defines a maximum body height from the upper body surface to the lower body surface, and the front plate defines a maximum plate height from the uppermost plate surface to the lowermost plate surface that is less than the maximum body height.

13. The system of claim 5, wherein the front plate defines a maximum plate height from the uppermost plate surface to the lowermost plate surface, and the one-piece body defines a maximum body height from the upper body surface to the lower body surface, wherein the maximum body height is substantially equal to or greater than the maximum plate height.

14. The system of claim 5, wherein the one-piece body further includes a first screw recess in communication with the front body surface and the upper body surface and a second screw recess in communication with the front body surface and the lower body surface, such that when the front plate is mounted to the one-piece body the first screw recess is aligned with one of the plurality of screw holes and the second screw recess is aligned with another of the plurality of screw holes.

15. The system of claim 5, wherein the recess is a through-hole that extends from the upper body surface to the lower body surface.

16. The system of claim 5, wherein at least one of the plurality of screw holes includes internal threads, and at least a portion of the head of one of the plurality of bone screws has a threaded portion that includes external threads configured to engage the internal threads of the one of the plurality of screw holes.

17. The system of claim 16, wherein the threaded portion is conically tapered.

18. The system of claim 5, further comprising a securing plate operatively connectable to the front plate in a manner to at least partially contain the head of at least one of the plurality of bone screws receivable in one of the plurality of screw holes between the front plate and the securing plate.

19. The system of claim 18, wherein the securing plate is fastenable to the front plate by at least one of a screw connection, a bayonet catch or a click catch.

20. The system of claim 5, further comprising a securing plate operatively connectable to the front plate in a manner to at least partially cover at least two of the plurality of screw holes.

21. A spine stabilizing system configured to be inserted into an intervertebral space, the spine stabilizing system comprising:
(a) a plurality of bone screws each having a shaft and a head that is connected to the shaft, each of the shafts being elongate along a respective longitudinal central axis;
(b) a one-piece body defining a front body surface, a rear body surface opposite the front body surface, a left side surface, a right side surface opposite the left side surface, a lower body surface, an upper body surface spaced from the lower body surface in a first direction, a recess that extends from a first opening in the upper body surface to a second opening in the lower body surface, and a body hole configured to receive one of the plurality of bone screws,
wherein the one-piece body is configured such that when the spine stabilizing system is inserted into the intervertebral space: 1) the upper body surface faces an endplate of a first vertebra; and 2) the lower body surface faces an endplate of a second vertebra; and (c) a front plate defining an uppermost plate surface, a lowermost plate surface opposite the uppermost plate surface, a front plate surface, a rear plate surface opposite the front plate surface, the front plate configured to be mounted to the one-piece body such that, the rear plate surface faces the front body surface; and 2) the first opening remains open to the first direction the front plate further defining a plurality of screw holes each configured to receive one of the plurality of bone screws such that the shaft of one of the plurality of bone screws passes through one of the plurality of screw holes, the body hole and one of the endplates of the first and second vertebrae, each of the plurality of screw holes defining a respective central axis, at least two of the plurality of screw holes extending through the front plate so that the central axis of each of the at least two of the plurality of screw holes is at an oblique angle relative to the rear plate surface, at least a portion of the uppermost plate surface configured to be disposed within the intervertebral space when the front plate is mounted to the one-piece body and the one-piece body is disposed within the intervertebral space, wherein the front plate is devoid of screw holes with an opening that 1) is positioned in the front plate surface and 2) has a center that is positioned beyond the first opening with respect to the first direction when the front plate is mounted to the one-piece body.

22. The system of claim 21, further comprising a securing plate operatively connectable to the front plate in such a manner to at least partially cover at least one of the plurality of screw holes.

23. The system of claim 21, wherein at least one of the plurality of screw holes includes internal threads.

24. The system of claim 21, wherein at least one of the plurality of bone screws includes external threading at least partially on the head.

25. The system of claim 21, wherein the front plate defines a maximum plate height from the uppermost plate surface to the lowermost plate surface, the one-piece body defines a maximum body height from upper body surface to the lower body surface, and the maximum plate height is substantially equal to the maximum body height.

26. The system of claim 21, wherein the one-piece body defines a middle plane equidistantly spaced between the upper body surface and the lower body surface, and the front plate is mountable to the one-piece body such that the central axis of each of the at least two of the plurality of screw holes defines a respective angle ranging from about 20° to about 60° relative to the middle plane.

27. The system of claim 21, wherein the one-piece body defines a middle plane equidistantly spaced between the left and right side surfaces, the middle plane extends from the front surface to the rear surface, and the front plate is mountable to the one-piece body such that the respective longitudinal central axis of each of the plurality of bone screws inserted into one of the plurality of screw holes defines a respective angle ranging from about 10° to about 45° relative to the middle plane.

28. The system of claim 26, wherein the middle plane is a first middle plane, and the one-piece body defines a second middle plane equidistantly spaced between the left and right side surfaces, the second middle plane extends from the front plate surface to the rear body surface, and the front plate is mountable to the one-piece body such that the respective longitudinal central axis of each of the plurality of bone screws defines a respective angle ranging from about 10° to about 45° relative to the second middle plane.

29. The system of claim 21, wherein the oblique angle between the axis of each of the at least two of the plurality of screw holes and the rear plate surface of the front plate is from about 30° to about 70°.

30. The system of claim 21, wherein an entirety of the uppermost plate surface is configured to be disposed within the intervertebral space when the front plate is mounted to the one-piece body and the one-piece body is disposed within the intervertebral space.

31. The system of claim 21, wherein the one-piece body is at least partially formed of plastic, the front plate is at least partially formed of a metallic material, and the at least two of the plurality of screw holes include a first angled screw hole and a second angled screw hole, the first angled screw hole angled in the front plate toward the uppermost plate surface, and the second angled screw hole angled in the front plate toward the lowermost plate surface.

32. The system of claim 21, wherein the lower body surface is spaced from the upper body surface in a second direction, and the one-piece body and the front plate are both devoid of screw holes positioned beyond the second opening with respect to the second direction.

33. The system of claim 21, wherein the front plate comprises a biocompatible, non-bone material.

34. The system of claim 21, wherein the first opening includes an outer perimeter that is defined entirely by the upper body surface.

35. A spine stabilizing system configured to be inserted into an intervertebral space, the spine stabilizing system comprising:
  a plurality of bone screws each having a shaft and a head that is connected to the shaft, each of the shafts being elongate along a respective longitudinal central axis;
  a one-piece body configured to be inserted between an endplate of a first vertebra and an endplate of a second vertebra, the one-piece body having a convex upper surface that is configured to face the endplate of the first vertebra, a convex lower surface configured to face the endplate of the second vertebra, a front body surface, a rear body surface, a right side body surface and a left side body surface spaced from the right side body surface along a lateral direction, and a portion of the one-piece body that is continuous along the lateral direction from the left side body surface to the right side body surface, the one-piece body defining a middle plane disposed equidistantly between the convex upper surface and the convex lower surface, the convex upper surface spaced from the convex lower surface in a first direction, the one-piece body defining a recess that extends at least into the convex upper surface such that the recess defines an opening that is open to the first direction; and
  a front plate defining a front plate surface and an opposed rear plate surface, the front plate configured to be mounted to the one-piece body such that the rear plate surface overlies the front body surface, the front plate having a plurality of screw holes, each of the plurality of screw holes configured to receive one of the plurality of bone screws, each of the plurality of screw holes defining a central axis, at least two screw holes of the plurality of screw holes 1) include an opening in the front plate surface that is positioned between the left side body surface and the right side body surface with respect to the lateral direction; and 2) extend through the front plate so that the central axis of each of the at least two screw holes is at an oblique angle relative to the middle plane, wherein the one-piece body is devoid of screw holes with an opening that is positioned beyond the opening of the recess with respect to the first direction, and the front plate is devoid of screw holes with an opening that 1) is positioned in the front plate surface and 2) has a center that is positioned beyond the opening of the recess with respect to the first direction when the front plate is mounted to the one-piece body.

36. The system of claim 35, wherein the oblique angle between the central axis of each of the at least two of the plurality of screw holes and the middle plane is from about 20° to about 60°.

37. The system of claim 35, wherein the convex lower surface defines a second opening that faces in a second direction that is opposite the first direction, and the one-piece body and the front plate are both devoid of screw holes positioned beyond the second opening with respect to the second direction.

38. The system of claim 37, wherein the one-piece body defines a recess that extends from the opening in the convex upper surface to the second opening in the convex lower surface.

39. A bone stabilizing system comprising:
a plurality of bone screws each having a shaft and a head that is connected to the shaft, the shaft defining a longitudinal central axis;
an integral one-piece body configured to be inserted between an endplate of a first vertebra and an endplate of a second vertebra, the one-piece body having an upper body surface configured to abut the endplate of the first vertebra, a lower body surface configured to abut the endplate of the second vertebra, and a front body surface, the front body surface defines a maximum body height from the upper body surface to the lower body surface; and
a front plate defining an uppermost plate surface and an opposed lowermost plate surface, the front plate defining a front plate surface and an opposed rear plate surface, the front plate defines a maximum plate height from the uppermost plate surface to the lowermost plate surface, such that the maximum plate height is less than the maximum body height, the front plate configured to be mounted to the one-piece body such that the rear plate surface is adjacent to and at least partially overlies the front body surface, the front plate having a plurality of screw holes each configured to receive one of the plurality of bone screws, the plurality of screw holes extending through the front plate and having an axis, at least two of the plurality of screw holes extending through the front plate at an angle relative to the rear plate surface of the front plate so that the axis of the respective screw hole ranges from about 30° to about 70°;
wherein at least a portion of the uppermost plate surface is configured to be disposed between the endplates of the first and second vertebrae when the front plate is mounted to the one-piece body and the one-piece body is disposed between the endplates of the first and second vertebrae.

40. The system of claim 39, wherein:
the one-piece body is at least partially formed of plastic and the front plate is at least partially formed of a metallic material;
the at least two screw holes include a first angled screw hole and a second angled screw hole, the first angled screw hole angled in the front plate toward the uppermost plate surface, the second angled screw hole angled in the front plate toward the lowermost plate surface; and
the front plate defines an uppermost plate surface and an opposed lowermost plate surface, at least a portion of the uppermost plate surface is configured to be disposed between the endplates of the first and second vertebrae when the front plate is mounted to the one-piece body and the one-piece body is disposed between the endplates of the first and second vertebrae.

41. The system of claim 39, further comprising a securing plate operatively connectable to the front plate in a manner to at least partially contain at least one of the heads of the plurality of bone screws receivable in one of at least two of the plurality of screw holes between the front plate and the securing plate.

42. The system of claim 39, wherein the upper body surface is spaced from the lower body surface in a first direction, and the one-piece body defines an opening that extends at least into the upper body surface such that the opening is open to the first direction.

43. The system of claim 42, wherein the front plate is devoid of screw holes positioned beyond the opening with respect to the first direction when the front plate is mounted to the one-piece body.

* * * * *